Figure 1:
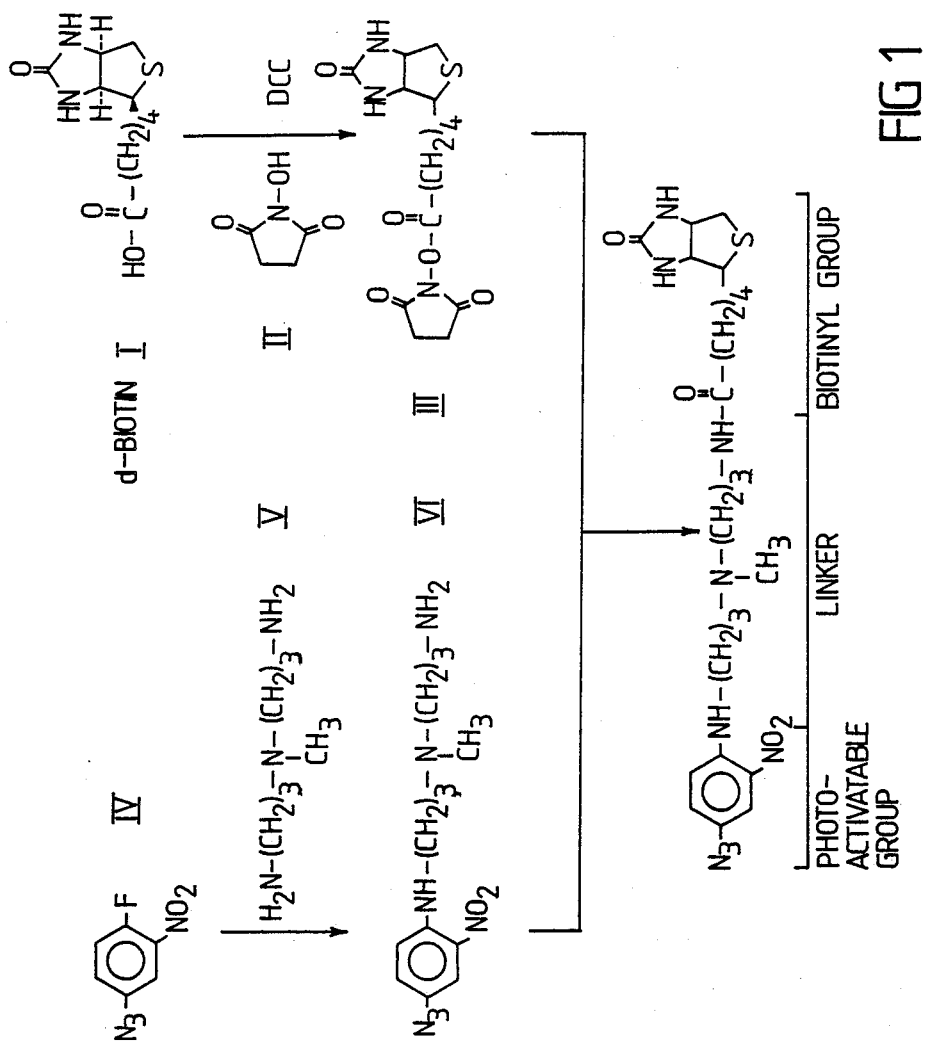

United States Patent [19]

Symons

[11] Patent Number: 4,898,951
[45] Date of Patent: Feb. 6, 1990

[54] COMPOUNDS USED AS INTERMEDIATES IN THE PREPARATIONS OF NON-RADIOACTIVE BIOLOGICAL PROBES

[75] Inventor: Robert H. Symons, Adelaide, Australia

[73] Assignee: Bresatac Limited, Adelaide, Australia

[21] Appl. No.: 191,811

[22] Filed: May 4, 1988

Related U.S. Application Data

[63] Continuation of Ser. No. 712,705, Mar. 15, 1985, abandoned.

[30] Foreign Application Priority Data

Mar. 22, 1984 [AU] Australia .............................. PG4200
Oct. 4, 1984 [AU] Australia .............................. PG7500

[51] Int. Cl.$^4$ .................. C07D 495/04; C07C 117/00
[52] U.S. Cl. ........................................ 548/303; 552/8; 435/6
[58] Field of Search ......................... 548/303; 260/349; 552/8

[56] References Cited

U.S. PATENT DOCUMENTS 4,282,287 1/1980 Giese .................................. 428/407
4,487,838 12/1984 Hynes et al. ..................... 548/545 X

FOREIGN PATENT DOCUMENTS 0119448 9/1984 European Pat. Off. .
0127438 12/1984 European Pat. Off. .
83/02277 7/1983 World Int. Prop. O. .
84/03285 7/1984 World Int. Prop. O. .

OTHER PUBLICATIONS

Nielsen et al., Reagents for Photoaffinity Labelling—Experientia 39 (1983); pp. 1063–1072.
Forster et al., Non-Radioactive Hybridization—Nucleic Acid Research, 13 (1985), pp. 745–761.
The Journal of Biological Chemistry, vol. 256, No. 2, Issue of Jan. 25, 1981, p. 761 by George Orr.
Affinity Chromatography and Gel Permeation, p. 42 (date unknown).

Primary Examiner—Joseph Paul Brust
Attorney, Agent, or Firm—Ladas & Parry

[57] ABSTRACT

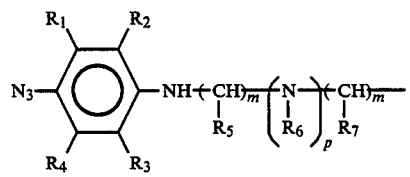

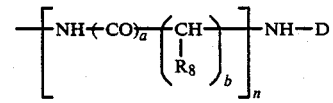

wherein $R_1$ to $R_4$, which may be the same or different, are selected from the group consisting of H, alkyl of 1 to 5 carbon atoms, $NO_2$, halogen, —COOH, or —$NH_2$;
wherein $R_5$, $R_6$, $R_7$, $R_8$ which may be the same or different are selected from the group consisting of H, alkyl of 1 to 5 carbon atoms and halogen; wherein
n is an integer of 0 to 5
m is an integer of 1 to 10
p is an integer of 0 to 1
a is an integer of 0 to 1
b is an integer of 1 to 10,
wherein if a is 1 then b is 1, and
wherein the moiety (Abstract continued on next page.)

PHOTOBIOTIN, VII includes at least 5 carbon atoms and wherein D is selected from the group consisting of
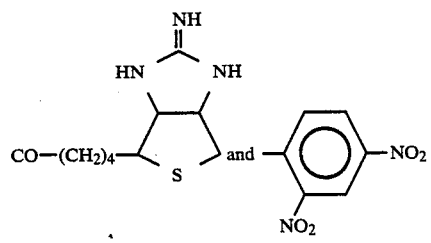
The compounds may be used as intermediates in the preparation of non-radioactive biological probes.
8 Claims, 4 Drawing Sheets

PHOTOBIOTIN, VII

COMPOUNDS USED AS INTERMEDIATES IN THE PREPARATIONS OF NON-RADIOACTIVE BIOLOGICAL PROBES

This is a continuation of co-pending application Ser. No. 712,705, filed on Mar. 15, 1985, now abandoned.

This invention relates to non-radioactive biological probes, their preparation and techniques using such probes, e.g. for the detection, localization and isloation of polynucleotides.

In biotechnology, labelled nucleic acid probes have become an indispensible tool for the detection and in situ localization of specific nucleic acid sequences. The probes have a significant commercial potential; a major application, for example, is likely to be in the diagnosis of human, animal and plant diseases.

Essentially, nucleic acid probes comprise a nucleotide sequence selected to hybridize with a complementary sequence of the nucleic acid which is of interest. The probe sequence is itself linked to a group which can be distinctly labelled in a way which facilitates convenient and reliable detection and assay.

However there are a number of disadvantages in the prior art. Traditionally, nucleic acid probes have been labelled with radioisotopes such as $^3$H, $^{32}$P, $^{14}$C or $^{125}$I. Although isotopic labelling offers extreme sensitivity, there are unfavourable cost, safety and stability factors inherent in the use of radioactive materials which have stimulated interest in the development of cheaper and more easily managed labelling techniques. As a result, DNA probes have recently become available in which the nucleotide sequence is linked to biotin (Vitamin H) (e.g. J. J. Leary, D. J. Brigati and D. C. Ward, 1983, Proc. Natl. Acad. Sci. USA 80, 4045–4049). The particular suitability of biotin as a probe ligand resides in the fact that after the biotinylated probe has hybridized with the polynucleotide under investigation indicator groups, such as enzymes, fluorescent molecules and chemiluminescent catalysts may be readily attached via avidin, an egg white protein which is known to bind specifically and very strongly with biotin. Alternatively, the biotinylated nucleic acid may be detected using antibiotin antibodies. A general review on the use of the avidin biotin complex as a tool in molecular biology is given by E. A. Bayer and M. Wilchek (1980) "Methods of Biochemical Analysis" 26, 1–45.

Whilst such probes provide certain advantages, the preparation of biotinylated DNA probes by known methods such as those of P. R. Langer, A. A. Waldrop and D. C. Ward (1981; Proc. Natl. Acad. Sci. USA 78, 6633–6637), D. J. Brigati, D. Myerson, J. J. Leary, B. Spanholz, S. Z. Travis, C. K. Y. Fong, G. D. Hsiung and D. C. Ward, (1983, Virology 126, 32–50) and J. J. Leary, D. J. Brigati and D. C. Ward (1983, Proc. Natl. Acad. Sci. USA 80, 4045–4049) involves the enzymic incorporation of biotinylated dUTP analogues into DNA by the well established nick translation reaction (P. W. J. Rigby, M. Dieckmann, C. Rhodes and P. Berg, 1977, J. Mol. Biol. 113, 237–251), which requires double-stranded DNA as substrate, or by the addition of a 3′-extension to single-stranded DNA using the enzyme terminal transferase.

There are a number of disadvantages to the enzymic incorporation of biotinylated nucleotides into nucleic acids. Single-stranded DNA cannot be used for nick translation because the bacterial DNA polymerase used in this procedure requires a complementary DNA strand, and hence double-stranded DNA, as a template. Although several bacterial and animal cell and animal viral RNA polymerase can use biotinylated dUTP analogues as substrates, the widely used avian virus reverse transcriptase cannot (Langer et al. 1981). In addition, biotinylated UTP analogues work with only low efficiency with bacterial RNA polymerases and are utilized poorly or not at all by eukaryotic RNA polymerases (Langer et al, 1981). Furthermore, the preparation of large amounts (milligram quantities) of biotinylated DNA probes for diagnostic kits requires large volume enzymic reactions which are expensive in terms of enzymes and substrates.

Biotin has been chemically linked to RNA via the protein cytochrome c using formaldehyde (J. E. Manning, N. D. Hershey, T. R. Broker, M. Pellegrini, H. K. Mitchell and N. Davidson, 1975, Chromosoma 53, 107–117) but this procedure has a number of disadvantages. The method takes two to three days to complete and is not readily applicable to less than about five micrograms of RNA; the cytochrome c-RNA linkage is unstable under hybridization conditions (Pellegrini, D. S. Holmes and J. Manning, 1977, Nucleic Acids Res. 4, 2961–2973); and the properties of the RNA may be significantly modified by the linkage of one bulky cytochrome c per 130 nucleotide residues aimed for in the published procedure.

Accordingly it is an object of the present invention to overcome, or at least alleviate, one or more of the difficulties related to the prior art.

Accordingly in a first aspect of the present invention there is provided a compound of the formula I:

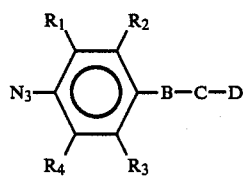

wherein
B is an —NH-group linking the group C to the benzene ring which is in the para position relative to the azide group;
C is an hydrocarbyl amine moiety including at least five carbon atoms;
D is a ligand or hapten; and
$R_1$ to $R_4$, which may be the same or different, are selected from H, alkyl of 1 to 5 carbon atoms, $NO_2$, halide group, carboxylic acid group or amino group, and acid addition salts thereof.

The novel compounds of formula I have been found to be useful intermediates in the preparation of nucleic acid probes.

Preferably B is a —NH-group in the para position relative to the azide group. More preferably, the hydrocarbyl amine moiety C is selected from

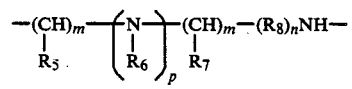

wherein
$R_8$ is

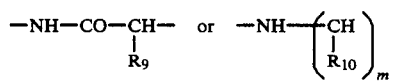

$R_5$, $R_6$, $R_7$, $R_9$, $R_{10}$ may be the same or different are selected from alkyl of 1 to 5 carbon atoms or halide group;

n is an integer of 0 to 5
m is an integer of 1 to 10
p is an integer of 0 to 1.

In a preferred form C is selected from the groups

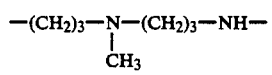

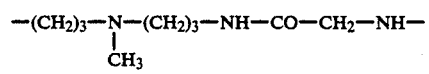

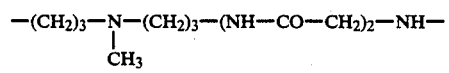

In a preferred embodiment, the hapten or ligand D is a moiety which, when coupled to a nucleic acid, is capable of forming a detectable complex with a peptide protein or other molecule, or which enables the labelled polynucleotide to be selectively extracted from unlabelled polynucleotides. The moiety D may be selected from biotin, imino biotin, or a dinitrophenol (DNP) group; or derivative thereof.

In general, highly reactive functional groups are required for the stable, chemical modification of nucleic acids. This poses two problems. Firstly, a prerequisite for the synthesis of a reagent is that the reactive group must not react with the ligand (the biotinyl moiety); hence, it was considered that many of the possible highly reactive groups could not be used. Secondly, cationic salts of nucleic acids, which are sparingly soluble in all but very polar solvents, are usually dissolved in aqueous solvents which are expected to drastically out-compete with the nucleic acid for reaction with most of the highly reactive groups.

The present invention overcomes the first problem with an aryl azide. Aryl azides are stable in the dark and can be photoactivated in situ to generate highly reactive aryl nitrenes. In particular, 4-fluoro-3-nitrophenyl azide is preferred because it can be readily coupled to amines (see below) and can be photoactivated with visible light thus avoiding irradiation with ultra-violet light which may damage the nucleic acid probe.

The present invention overcomes the second problem by selecting a linker containing a basic tertiary amino group which is positively charged at neutral pH. This gave the reagent a high solubility in water and an electrostatic attraction for nucleic acids, thus enabling the use of a high local concentration of the reagent in the vicinity of the nucleic acid. A long linker was found to be necessary to allow the biotinyl group of the biotin-labelled nucleic acid to efficiently penetrate the biotin-binding sites within avidin. Hence, a long symmetrical tri-amine suitable for synthetic reactions is preferred. In a preferred form, the compounds of formula I are those in which $R_1$ to $R_4$ are hydrogen. Alternatively, $R_1$, $R_2$, and $R_4$ may be hydrogen and $R_3$ may be $-NO_2$.

Particularly preferred compounds according to formula I are as follows:

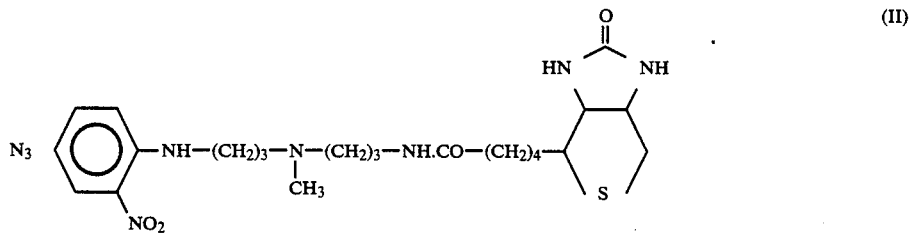

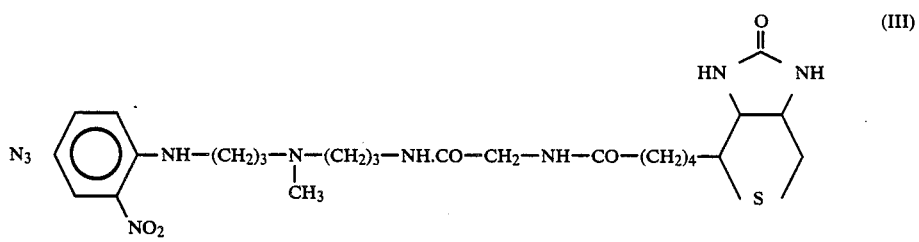

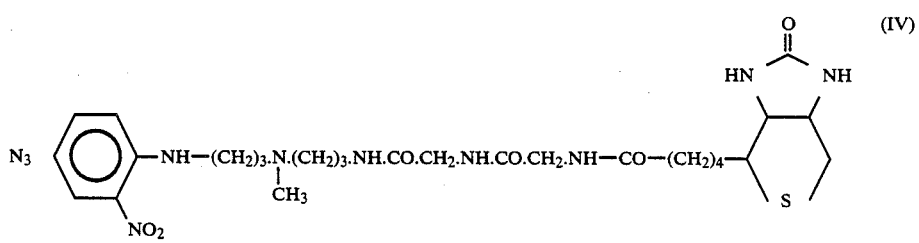

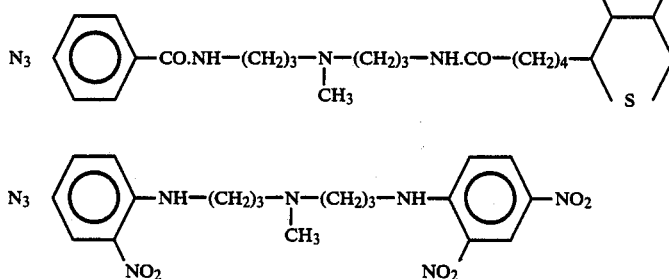

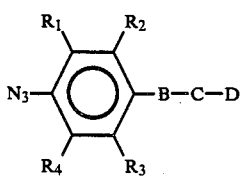

For convenience these compounds are referred to as photobiotin 14 (because, in use, the biotin moiety is coupled to a nucleic acid via a chain 14 atoms long), photobiotin 17, photobiotin 20, denitro-photobiotin 14 and photo-DNP, respectively. Photobiotin 14, N-(4-azido-2-nitrophenyl)-N'-(N-D-biotinyl-3-aminopropyl)-N'-methyl-1,3-propane diamine, is water soluble as the acetate salt, stable in aqueous solution in the absence of light and is rapidly photolysed by visible light to convert the azido group to a highly reactive nitrene which form stable linkages to nucleic acid residues. The nitrene can also couple to other polymeric substances such as proteins and carbohydrates and such applications are included in the scope of the present invention.

In the structural formula above, -B-C- may be a residue of water-soluble, symmetrical amine containing a quaternary group. This may function to impart hydrophilic qualities to the compound and to promote ionic inter-reaction to polyanionic nucleic acids. The inclusion of one or more glycine residues as illustrated in formulas III and IV, function to lengthen the linker arm between the nucleic acid and the ligand or hapten.

Other amines, e.g. spermidine, $NH_2.(CH_2)_3.NH.(CH_2)_4.NH_2$, and spermine, $NH_2.(CH_2)_3.NH(CH_2)_4.NH.(CH_2)_3.NH_2$, can be used for -B-C of formula I to give linker arms between biotin and nucleic acid of 15 atoms and 19 atoms, respectively. These amines together with the lengthened amines in formulae III and IV and other amines of a similar nature fall within the scope of this invention.

The present invention further includes the acid addition salts of the compounds of formula I described above. The hydrogen acetate and hydrogen formate salts are preferred. The acid addition salts are useful intermediates as they provide extended shelf lives if kept in the dark.

In a further aspect of the present invention there is provided a process for the preparation of a compound of the formula I:

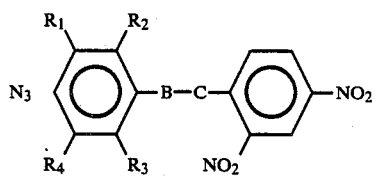

wherein

B is an —NH-group linking the group C to the benzene ring which is in the para position relative to the azide group;
C is an hydrocarbyl amine moiety including at least five carbon atoms;
D is a ligand or hapten with the proviso that D is not a dinitrophenol group; and
$R_1$ to $R_4$, which may be the same or different, are selected from H, alkyl of 1 to 5 carbon atoms, $NO_2$, halide group, carboxylic acid group or amino group; and acid addition salts thereof; which process includes reacting a compound of the formula VII

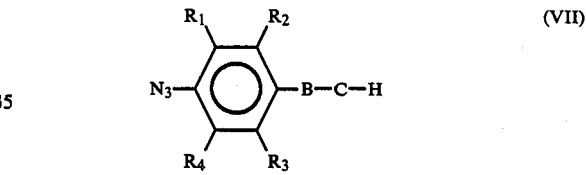

with a compound of the formula VIII.

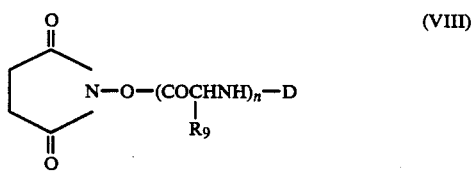

In a further aspect there is provided a process for the preparation of a compound of the formula

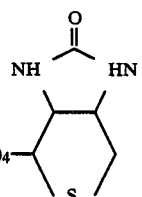

wherein
B is an —NH-group linking the group C to the benzene ring which is in the para position relative to the azide group;
C is an hydrocarbyl amine moiety including at least five carbon atom;
$R_1$ to $R_4$, which may be the same or different, are selected from H, alkyl of 1 to 5 carbon atoms, $NO_2$, halide group, carboxylic acid group or amino group;

and acid addition salts thereof; which process includes reacting a compound of the formula VII

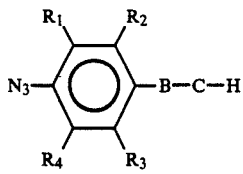
(VII)

wherein B, C and $R_1$ to $R_4$ have the meanings as defined above with a compound of the formula

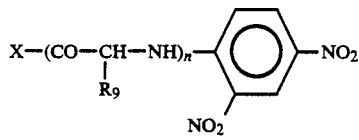
XIII wherein
X is a halide group;
$R_9$ is selected from H, alkyl of 1 to 5 carbon atoms or a halide group; and
n is an integer of 1 to 5.

Preferably the compound of formula XIII has the formula

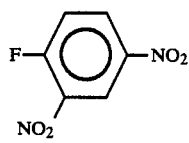

Preferably the compound of formula VII has the formula IX

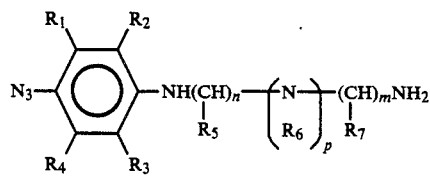
(IX)

and is prepared by reacting a compound of formula X

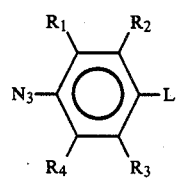
(X)

wherein L is a leaving group with a compound of formula XI

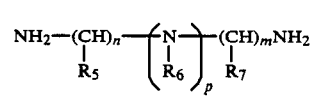
XI wherein $R_5$, $R_6$, $R_7$, m, n and p are as defined above.

More preferably the compound of the formula X is selected from 4-fluoro-3-nitrophenyl azide and N-((4-azidobenzyl)oxy)succinimide.

In a further preferred embodiment the compound of formula VIII is selected from the following:

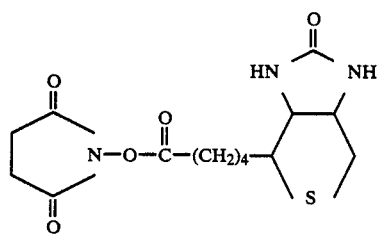

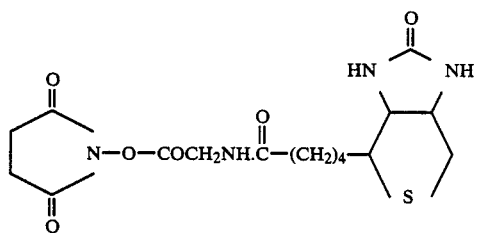

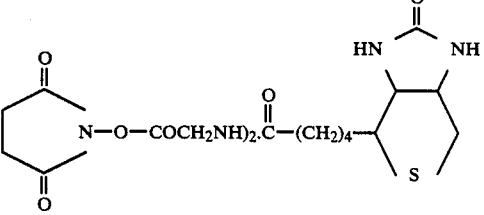

Photobiotin 14 (II) for example may be synthesized by the synthesis route illustrated in FIG. I.
The related compound having the structure:

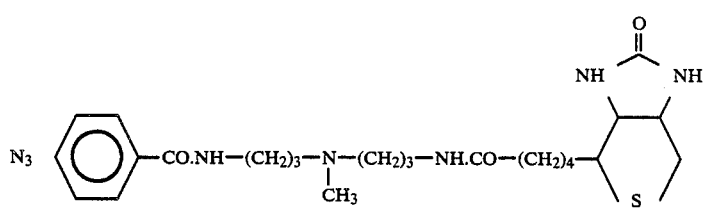

may be prepared in a similar way but using N-((4-azidobenzyl)oxy)succinimide instead of 4-fluoro-3-nitrophenyl azide at step (B). The above outlined preparative methods fall within the scope of the invention.

The reaction procedure as specified above allows flexibility in the preparation of the various photobiotins considered within the scope of this invention. For example amine IX can be replaced by spermidine, spermine or other diamino compounds, with or without a quaternary amino group. Further, biotinyl-N-hydroxysuccinimide ester (VIII) can be replaced by biotinyl-glycyl-N-hydroxysuccinimide ester or biotinyl-glycyl-glycyl-N-hydroxysuccinimide ester to produce photobiotins 17 and 20 (V and VI), respectively. In addition, the procedure allows the covalent coupling of ligands other than biotin or of haptens at Step (d) above to produce a range of photoactivatable agents suitable for the preparation of nucleic acid probes.

In a still further aspect of the present invention there is provided a compound of the formula XII:

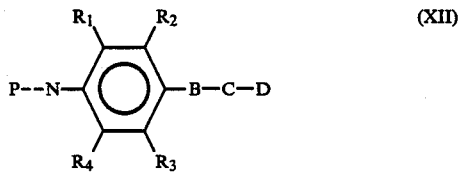

wherein

P is a residue of a polynucleotide chain, a protein or carbohydrate;

B is an —NH— group linking the group C to the benzene ring which is in the para position relative to the azide group;

C is an hydrocarbyl amine moiety including at least five carbon atoms;

D is a ligand or hapten; and $R_1$ to $R_4$, which may be the same or different, are selected from H, alkyl of 1 to 5 carbon atoms, $NO_2$, halide group, carboxylic acid group or amino group; and acid addition salts thereof.

Preferably, P is a residue of a single- or double-strand deoxyribonucleic (DNA) or ribonucleic acid (RNA). The compounds of formula XII may function as non-radioactive biological probes.

The residue P is selected to form, in use a detectable complex with a complementary nucleic acid sequence in a sample to be tested. The residue P may include a cloning vector. The cloning vector may be modified to include a nucleic acid sequence of interest. This may be achieved using known recombinant DNA techniques. Plus and minus recombinant DNA clones may be used. The residue P may be a single-strand bacteriophage M13 DNA containing a cloned insert. Single-strand, circular, phage M13 DNA probes are preferred for the following reasons: cloning into the replicative form of M13 allows the separate isolation of single-stranded clones of either strand of the inserted sequence; single-stranded probes hybridize to complementary sequences more efficiently than double-stranded probes; the M13 vector provides 7,200 residues of DNA in addition to the inserted sequence for labelling with biotin and for binding to avidin conjugates, thus increasing the sensitivity of detection of the probe; and M13 clones are widely used for DNA sequencing by the dideoxynucleotide chain-termination technique.

The use of reagents as described above to covalently couple a ligand (or hapten) to a polymer by chemical means has a number of advantages over the previously mentioned enzymatic procedures of Langer et al (1981), Brigati et al (1983) and Leary et al (1983). For example, referring specifically to photobiotin for sake of brevity, although it is to be understood that biotin is not the only instance of a ligand or hapten with which the following advantages can be enjoyed e.g. iminobiotin and dinitrophenol:

The synthesis of such reagents as the photobiotin compounds and their covalent coupling to nucleic acids, either single- or double-stranded, is rapid and straightforward. The chemical attachment of biotin is not restricted by the efficiency of incorporation of a nucleotide analogue by enzymes. Essentially one procedure can be used for labelling all nucleic acids (DNA or RNA) which eliminates the need for different enzymes and primers. It is easier and cheaper to label nucleic acids on a large scale. This is important for the preparation of biological probes for diagnostic kits or for use in liquid hybridization reactions where large amounts of probe may be required.

The ability of couple biotin to single-strand DNA offers a convenient route to probes of significantly enhanced, and in principle limitless, sensitivity. Thus, the DNA strand of interest, comprising say 200 nucleotide residues, might be inserted in single-strand phage M13 vector DNA of perhaps 7,000 nucleotide residues; biotin is the coupled to the vector/insert composite in the ratio of, say, one biotin to every 200 nucleotide residues. This extent of labelling of an insert interferes to only a minor degree with its ability to hybridize to complementary nucleic acid sequences, but the number of biotins available for detection has been increased 35-fold over what would have been available if only the DNA strand of interest had been employed.

Additional enhancement of the sensitivity of detection of the biotinylated nucleic acid probe after hybridization, may also be undertaken. For example, given that a double-strand linear DNA molecule of molecular weight $10 \times 10^6$ is photolysed with photobiotin to give a coupling rate of one biotin per 300 residues, then there would be a total of 100 biotin residues per DNA (total of 30,000 nucleotide residues). The complex used for the detection of the hybridized biotinylated nucleic acid probe is then prepared by the addition of one molecule of avidin-alkaline phosphatase (or peroxidase) conjugate per biotin coupled to the double-strand DNA. Since each avidin molecule has the potential to bind four molecules of biotin, this larger linear DNA-biotin-avidin-enzyme complex still has a large number of potential biotin binding sites available for binding to biotin residues on the hybridized biotinylated nucleic acid probe.

Theoretically, therefore, this procedure can give a further 100-fold enhancement in the sensitivity of detection of a hybridized nucleic acid probe. Taking this enhancement with that calculated above, there is a theoretical possible amplification of 3,500-fold over the sensitivity of detection given by a simple nucleic acid probe prepared by enzymic procedures and the use of monomeric avidin-enzyme conjugates. In practice, considerable enhancement of sensitivity is likely to be obtained but not at the calculated level since steric factors will limit the accessibility of the large enzyme complex to the hybridized biotinylated nucleic acid probe.

A single stranded probe is preferred over a double strand probe, since complementary sequences are present in solution and these will hybridize more rapidly with each other than with a complementary sequence in the test sample spotted on nitrocellulose. This means a lower efficiency of use of double-stranded probes compared to single-stranded ones.

The nucleic acid probes particularly preferred in diagnostic applications:

(i) Where disease agents cannot be detected by immunological methods e.g. the plant viroids which are RNA molecules without a protein coat and hence are non-immunogenic.

(ii) For disease agents which are difficult to detect by immunological methods. There are a number of these in the clinical field and also agricultural and this is where he first uses will be.

(iii) Where a nucleic acid probe approach will provide a method superior to the immunological methods in use.

Such disease agents include
(1) *Mycoplasma pneumoniae*
(2) Epstein Barr virus
(3) Cytomegalovirus
(4) Hepatitis B virus
(5) Non-cultivatable adenoviruses that cause e.g. gastro-enteritis
(6) Human T cell lymphoma virus
(7) Chlamydia.

According to a further aspect of the present invention there is provided a process for the preparation of a compound of formula XII

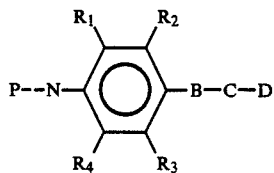

wherein P, B, C, D and $R_1$ to $R_4$ are as specified above which process includes
(1) providing
  (a) a compound of formula I

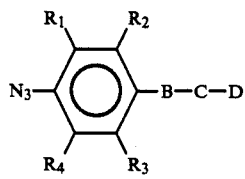

wherein B, C, D and $R_1$ to $R_4$ are as specified above and
(b) a probe sequence selected from nucleic acid carbohydrate or protein sequences,
(2) contacting (a) and (b); and
(3) subjecting the mixture of step (2) to a source of electromagnetic radiation for a period sufficient to cause reaction therebetween.

Preferably the probe sequence is a single or double strand sequence of deoxyribonucleic acid (DNA) or ribonucleic acid (RNA). Preferably step (2) comprises mixing (a) and (b) in solution. An approximately neutral solution may be used. The solution may be formed in any suitable solvent. Ethylene diamine tetraacetic acid (EDTA) is preferred. The mixture so formed may be sealed in a suitable container e.g. a capillary tube.

The mixture may be subjected to electromagnetic radiation at reduced temperature. A temperature of lower than about 5° C. is preferred. The electromagnetic radiation may take the form of visible light.

In a preferred form the process may further include
(4) removing unreacted components by solvent extraction.

An alcohol solvent extraction may be undertaken. Butan-2-ol may be used as the solvent.

Preferably, compounds of the formulae I may be coupled to probe-DNA sequences to give compounds of formula XII by, e.g., irradiating a neutral solution of the DNA plus photobiotin in dilute sodium EDTA with visible light at temperatures lower than about 5° C. After removal of unreacted components, e.g. by butan-2-ol extraction in the case of photolysed photobiotin, the assembled probes may then be used in the same way as traditional biotinylated probes in roles calling for the detection and localization of specific nucleic acid sequences, and such uses are considered to represent a further aspect of the present invention.

Thus in a further aspect the present invention provides a process for the detection and/or identification of a nucleic acid, protein or carbohydrate sequence which process includes
(1) providing
  (a) a sample to be tested and
  (b) at least one compound of the formula XII

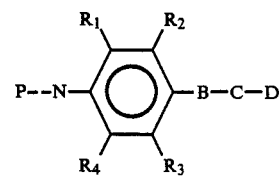

wherein P, B, C, D and $R_1$ to $R_4$ are as specified above,
(2) contacting (a) and (b) under conditions suitable for the formation of a complex therebetween and
(3) subjecting the product of step (2) to a detection and/or extraction process for the hapten or ligand D.

Preferably the sequence to be detected and/or identified is a nucleic acid sequence. It is possible to determine the presence of a specific DNA or RNA molecule, particularly such a molecule derived from a living organism, e.g. bacteria, fungus, virus, yeast, plant or animal. This in turn permits diagnosis of nucleic-acid-containing etiological agents or the like in a patient or other subject. The probe sequence P of formula XII accordingly selected is a single strand or double strand DNA or RNA sequence. In this form the complexing step (2) may be a hybridization of at least one nucleic acid probe to complementary nucleic acid sequences in the sample. The complementary nucleic acid sequences may be bound to a suitable solid support. The solid support may be a sheet of cellulose nitrate. Alternatively, glass beads, or polystyrene beads may be used as the solid support. Glass beads which have been derivatised to add a reactive amino group may be used. Polystyrene beads, also with a reactive amino group, are available commercially from Pierce Chemical Co. (U.S.).

The detection step (3) will depend on the selection of the hapten or ligand. Where biotin ligand is used the detection step (3) may comprise
(a) reacting the product of step (2) with an excess of an avidin-, streptavidin- or anti-biotin antibody-enzyme complex and
(b) extracting the product thereof. It will be understood that the detection method described above is analagous to the well-known enzyme-linked immunosorbent assay (ELISA) test. Examples of suitable enzymes which may be used in the detection step (3) include alkaline phosphatase and horse-radish peroxidase.

In an alternative embodiment wherein the hapten or ligand is 2,4-dinitrophenol, the detection step (3) may include
(a) reacting the product of Step (3) with a monoclonal or polyclonal antibody prepared against 2,4-dinitrophenol and
(b) extracting the product thereof. Such a detection method is similar to that described in relation to the biotin probe and may be conducted under standard enzyme-linked immunosorbent assay (ELISA) conditions.

In a preferred embodiment of this aspect of the present invention Step (1) of the process includes providing
(a) at least two compounds of formula XII wherein the hapten or ligand D on each compound is different; and wherein Step (3) includes
(a) subjecting the hydridisation product of Step (2) to a first extraction process for one hapten or ligand and
(b) subsequently subjecting the extraction product of (a) to a detection process specific to the second hapten or ligand.

It will be understood that the other of the nucleic acid probes is not removed from solution during this procedure unless it is hybridized to the same nucleic acid sequence as the probe which has been removed. The presence of the other probe bound to the solid support is then detected by a reaction specific to its ligand or hapten. A positive reaction indicates the presence in the nucleic acid test sample of the target nucleic acid.

In order to more fully explain the invention, but by way of example only, an embodiment of the invention is summarized in more practical detail as follows:

Recombinant DNA clones of the target nucleic acid specific for the diseased state are prepared in a single-strand phage M13 vector. The two clones to be used as probes are constructed in such a way that they hybridize to different, non-overlapping sections of the same molecule of the target nucleic acid. These two sections do not need to be contiguous but it is preferred that they are near to each other in case there is partial fragmentation of the target nucleic acid during its preparation for hybridization or during the hybridization reaction.

The two selected probes are photochemically labelled, one using photobiotin (I) and the other using photo-DNP (II), such that there are a number, preferably about 30 to 50, molecules of ligand of hapten attached to each molecule of DNA. Other pairs of ligands or haptens can be used as appropriate.

Equimolar amounts of the two labelled probes are then mixed with a nucleic acid extract under test for the target nucleic acid and the mixture hybridized under one phase liquid conditions. Hybridization is continued under appropriate conditions to ensure that the hybridization of the two probes to any target nucleic acid present has gone, or nearly gone, to completion. If the probes are well in excess of the target nucleic acid, then the reaction is essentially pseudo-first order and the rate of hybridization can be controlled by the concentration of the probes. This is an important consideration when the concentration of the target sequence is low as it will provide a detection system of high sensitivity.

The hybridized probes will be present in a hybrid structure of the type diagrammatically presented in FIG. II. The hybridization mixture is then added to a solid support e.g. a well of a plastic microtitre plate (as used in standard ELISA assays) which had previously been coated with antibody (either polyclonal or monoclonal) prepared against 2,4-dinitrophenol. Incubation for an empirically determined time under defined conditions will allow the absorption of all or most of the DNP-labelled probe from solution. This will include unhybridized probe as well as that hybridized to the target nucleic acid. The biotinylated DNA probe will not be removed from solution under these conditions unless it is also hybridized to the same piece of target nucleic acid as the DNP-labelled probes. All unbound material is then removed by thorough washing.

The next step is the specific detection of any hybridized biotinylated DNA probe present in each well. By analogy with detection systems widely used in ELISA assays, one approach is to use avidin or streptavidin covalently coupled to an enzyme or anti-biotin antibodies covalently coupled to an enzyme. Examples of suitable enzymes are alkaline phosphatase and horse-radish peroxidase. Hence, an avidin-, streptavidin or antibody-enzyme complex is added to each well and incubated under defined conditions to ensure binding to the bound biotin in each well. After thorough washing to remove excess enzyme reagent, the appropriate substrate is added and the plate incubated for colour development.

The presence of bound target sequence in any well is determined by colour development with the intensity of colour being related to the amount of bound target nucleic acid. The colour concentration can be determined using an automatic ELISA plate reader which provides a printed record.

An important feature of this embodiment of the present invention is the use of two non-radioactive biological probes which are labelled with different ligands or haptens and which hybridize to the same piece of target nucleic acid but not to each other. The target nucleic acid is specific for a specified diseased state in humans, animals or plants, where plants are taken to include all microorganisms. The method is not restricted to biotin and 2,4-dinitrophenol as in the example given hereinabove since these can be replaced by other ligands or haptens which can be detected using appropriate detection systems. Further, in the example given, where the microtitre plate is coated with avidin or streptavidin rather than with anti-DNP antibodies, detection of bound target sequence may be by use of anti-DNP antibodies coupled to a suitable enzyme.

The general procedure described in this preferred embodiment has a number of distinct advantages over other methods which use hybridization procedures for the detection and diagnosis of specific target nucleic acids. Most of the methods of the prior art use a solid phase, either for binding the target nucleic acid as in the dot-blot procedure and variants of it or for immobilizing a DNA probe as in the sandwich hybridization procedure. The advantages are as follows:

Hybridization in a single liquid phase is recognized to be about 10 times faster than in the two phase liquid-solid support system. Hence, hybridization times can be reduced considerably from the usual "overnight" period required for two-phase systems to several hours or less for the one-phase liquid system. Theoretically, hybridization time could be reduced to minutes by increasing the concentration of the two probes. The practical limit would be determined here by background reaction in control samples.

Large quantities of test sample can be used for the hybridization reaction. For example, it is possible to use 100 to 200 ul of test sample in the one phase system in contrast to the usual 5 ul spotted for dot-blot assays. This would give increased sensitivity of detection.

Once the initial hybridization reaction and binding to the solid support is completed, the rest of the protocol is essentially that of the ELISA procedure so that a variety of well-established detection methods and approaches can be used.

In an alternative embodiment two or more target nucleic acids may be detected in the one test sample. Only one hybridization reaction mixture is prepared but subsequent procedures allow the detection of two or more target nucleic acids. This is achieved by hybridization with a mixture of the appropriate pairs of probes for each target nucleic acid. One probe of each pair is labelled with the same ligand or hapten, e.g. biotin, while the other probe in each pair is labelled with a different ligand or hapten which has specific detection system, e.g., 2,4-dinitrophenol, (alternatives are given in B. F. Erlanger, 1980, Methods Enzymol. 70, 85–104). The hybridization solution is then distributed between a number of wells of a microtitre plate coated with avidin (or streptavidin). Different wells containing the same test sample would then be screened using detection systems specific for each of the haptens used.

In a further alternative embodiment the reverse approach may be preferred, that is each well is coated with a different antibody for each ligand or hapten rather than with the same material (avidin or streptavidin) in the example given. Hence each well would select out a different target nucleic acid but the detection system would be the same for each well since it would be detecting bound biotinylated DNA probes.

In a still further aspect of the present invention there is provided a diagnostic kit for detecting and/or identifying nucleic acid, protein or carbohydrate sequences in a sample, which includes a compound of formula XII

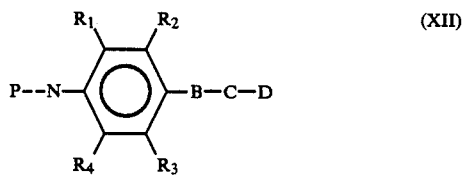

wherein
p is a residue of a polynucleotide chain, a protein or carbohydrate;
B is an —NH— group linking the group C to the benzene ring which in the para position relative to the azide group;
C is an hydrocarbyl amine moiety including at least five carbon atoms;
D is a ligand or hapten; and
$R_1$ to $R_4$, which may be the same or different, are selected from H, alkyl of 1 to 5 carbon atoms, $NO_2$, halide group, carboxylic acid group or amino group; and acid addition salts thereof.

The diagnostic kit may further include an avidin-streptavidin- or antibody-enzyme complex. A streptavidin, biotinylated polymer of calf intestinal alkaline phosphatase or a streptavidin-biotinylated acid phosphatase complex may be used.

The diagnostic kit may also include colorimetric agents. The colorimetric agents may include a phosphate compound and an indicator compound. The phosphate compound may be selected from 5-bromo-4-chloro-3-indolyl phosphate and naphthol AS-MX phosphate. The indicator compound may be selected from nitro blue tetrazolium and fast violet B salt.

The present invention will be more fully described with reference to the accompanying examples. It should be understood that the following discussion is illustrative only and should be not taken in any way as a restriction on the generality of the invention as described above.

MATERIALS AND METHODS

Materials

Avidin, d-biotin, N-hydroxysuccinimide, 5-bromo-4-chloro-3-indolyl phosphate, nitro blue tetrazolium and avidin-bovine intestinal alkaline phosphatase conjugate (2.1 mole alkaline phosphatase/mole avidin) were obtained from Sigma. N,N'-dicyclohexylcarbodiimide (DCC) was from Mann Research Laboratories. 4-Fluoro-3-nitroaniline and N-(3-aminopropyl)-N-methyl-1,3-propanediamine [N,N-bis(3-aminopropyl)methylamine] were from Tokyo Kasei. Kieselgel 60 F254 and aluminiumoxid 60 F254 TLC plates were from Merck. Kits for the detection of biotin-labelled DNA were from Enzo Biochem (Detek 1-ACP, #EBP-821) and Bethesda Research Laboratories (BRL, #8239SA). Pyridine was distilled twice from ninhydrin and once from $CaH_2$. Plus and minus recombinant DNA clones of the 247 residue, single-stranded RNA of avocado sunblotch viroid (ASBV) containing full-length inserts in the single-stranded M13mp93 DNA vector were constructed and purified as in Barker et al. Journal of virological Methods 10 (1985) 87–98.

Synthesis of N-(3-Aminopropyl)-N'-(4-azido-2-nitrophenyl)-N-methyl-1,3-propanediamine (VI)

All reactions involving the formation and use of aryl azides were carried out in the dark. 4-Fluoro-3-nitrophenyl azide (IV) was synthesized by the method of Fleet et al. (1972) Biochem. J. 128 449–508 except that 32 ml of conc. HCl-water solvent (5:3, v/v) were used per gram of 4-fluoro-3-nitroaniline, and the first two filtrations were not required. A solution of 4-fluoro-3-nitro-phenyl azide (0.91 g, 5.0 mmol) in dry ether (10 ml) was added with stirring to a solution of N-(3-aminopropyl)-N-methyl-1,3-propanediamine (V; 3.2 ml, 20 mmol) in dry ether (20 ml) and the mixture was stirred for 30 min. TLC on alumina with methanol showed the reaction to be complete. The solvent was removed and the red oil was dissolved in water (25 ml). 1M NaOH (25 ml) was added and the product was extracted into ethyl acetate (2×50 ml). Although the aqueous phase was still dark red, less than 5% of the product remained. Analysis of the extract by TLC on silica with acetic acid-water (1:9, v/v), using ninhydrin to detect amines, showed the product to be free of compound V. The pooled ethyl acetate extracts were dried over $Na_2SO_4$ and the solvent was removed to give the crude product which was used without further purification.

Synthesis of N-(4-Azido-2-nitrophenyl)-N'-(N-d-biotinyl-3-aminopropyl)-N'-methyl-1,3-propanediamine (Photobiotin, VII)

d-Biotinyl-N-hydroxysuccinimide ester (III) was synthesized from d-biotin (I) by the DCC method of Bayer and Wilchek (1980) "Methods of Biochemical Analysis" 26, 1–45 except that the ester was isolated by precipitation from ether and used without further purification. N-(3-Aminopropyl)-N'-(4-azido-2-nitrophenyl)-N-methyl-1,3-propanediamine (VI; approx. 5 mmol) was dissolved in a solution containing d-biotinyl-N-hydroxysuccinimide ester (1.7 g, 5.0 mmol) in pyridine-water (7:3 v/v, 50 ml), and the solution was incubated at 37° C. for 2 h. TLC on alumina with tetrahydrofuran-water (19:1; v/v) showed the reaction to be complete. The solvent was removed and the residue was dissolved in a mixture of 0.5M NaHCO$_3$ (100 ml) and 2-butanol (100 ml). The large volume was necessary to visualize the interface between the phases. The 2-butanol layer was removed, washed successively with water (100 ml) and saturated NaCl (100 ml), and then slowly added to ether (900 ml). The suspension was stirred, the red precipitate was allowed to settle, and the supernatant was decanted. The precipitate was washed with ether (100 ml) and dried in vacuo to give the product (1.33 g, 50% yield from 4-fluoro-3-nitrophenyl azide), m.p. 114.5°–115° C. (corrected). % Elemental analysis calculated for $C_{23}H_{35}N_9O_4S$: C 51.8, H 6.6, N 23.6. % Found: C 50,6 H 6.8, N 23.4 (Australian Mineral Development Laboratories). TLC on alumina with methanol showed the product to be a single spot with $R_F$ 0.75 (the symmetrical disubstitution product formed from compounds IV and V has $R_F$ 0.6). TLC on silica with acetonitrile-water (19:1, v/v), using p-dimethylaminocinnamaldehyde spray to detect biotin derivatives (21), showed the product to be free of compounds I, II and III. Photobiotin is poorly soluble in water.

Preparation of the Hydrogen Acetate Salt of Photobiotin (Photobiotin Acetate)

Figure 2:
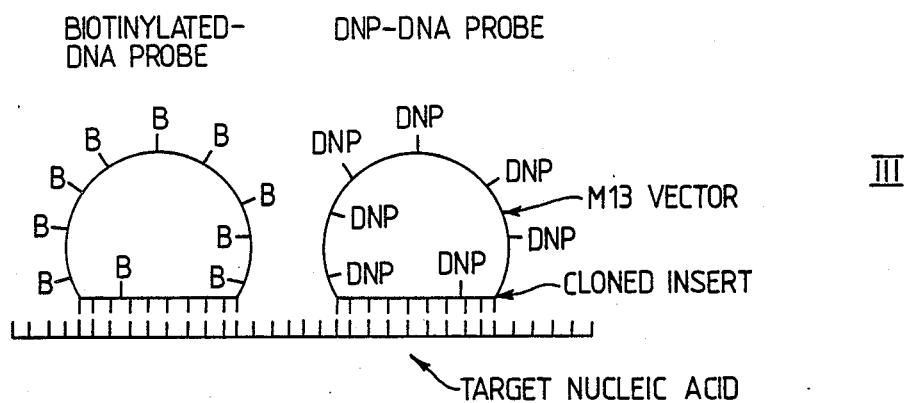

A solution of photobiotin (0.11 g, 0.21 mmol) in 1M acetic acid (0.30 ml) was lyophilized to remove excess acetic acid. The resulting hygroscopic, red solid is very water-soluble, with $_{max}$(water)=261 and 473 nm (M=19,200 and 3,900$M^{-1}cm^{-1}$; see FIG. 2). Solutions of photobiotin acetate in water are stable in the dark at −15° C. for at least five months.

Synthesis of N-(4-Azido-2-nitrophenyl)-N'-(N-2,4-dinitrophenyl-3-aminopropyl)-N'-methyl-1,3-propanediamine (Photo-DNP)

Crude N-(3-aminopropyl)-N'-(4-azido-2-nitrophenyl)-N-methyl-1,3-propane diamine (300 mg, approx. 1 mmol) was dissolved with stirring at room temp. in 70% pyridine-water (5 ml). A solution of 1-fluoro-2,4-dinitrobenzene (110 mg, 1 mmol) in 70% pyridine water (5 ml) was added in one portion with stirring. An orange red precipitate began to form at once and the reaction mix was stirred at room temp. overnight. The mixture was then concentrated on a rotary evaporator to an oil which was dissolved in CH$_2$Cl$_2$ (20 ml), washed with 1M NaOH (20 ml), dried over Na$_2$SO$_4$ and again concentrated on a rotary evaporator to give an oily solid. Last traces of solvent were removed by evacuation with an oil pump at room temp. to give photo-DNP as an orange-red powder. Yield was 294 mg. M.p. 90°–95° C. TLC on alumina with dichloroethane was solvent showed the product to be a single spot with $R_f$ 0.6; under these conditions, the starting amine remained at the origin.

Preparation of Formate Salt of Photo-DNP (Photo-DNP formate)

Photo-DNP (9 mg) was treated with 1M formic acid (200 ul). When all the solid had dissolved, the orange-red solution was evaporated on a rotary evaporated and then with an oil pump. The residue of photo-DNP acetate was dissolved in water (9 ml) and stored at −15° C. In water, λmax=261 and 358 nm.

Preparation of DNP-DNA-Reaction of Photo-DNP with phage M13 DNA

Single-stranded M13 DNA (1 ug/ml) and photo-DNP (0.5 ug/ml) in 0.1 mM EDTA were irradiated with visible light for 15 min at 0° C. while sealed in a glass capillary. The solution was diluted to a final concentration of 0.1M Na$_2$CO$_3$ or 0.1M NaOH and extracted three times with an equal volume of ethyl acetate. The aqueous phase was made to 1M Na acetate, pH 5.2, with 5M buffer and the DNA precipitated by the addition of 2.5 vol. cold ethanol and storage at −20° for 2 hours. A red precipitate of DNP-DNA was obtained on centrifugation. Control experiments showed that the unreacted photolysed photo-DNP was removed by this purification procedure.

Preparation of anti-DNP antibodies (polyclonal)

These were prepared by standard procedures. DNP groups were coupled to bovine serum albumin via 1-fluoro-2,4-dinitrobenzene and the DNP-protein injected into rabbits. Collected serum was fractionated with 30% saturated ammonium sulphate and the precipitate after desalting was used as a source of antibodies.

Labelling of Nucleic Acids with Photobiotin Acetate

In very subdued light, a solution of photobiotin acetate (1 ug/ul) in water (1–25 ul) was added to an equal volume of nucleic acid (1 ug/ul) in water or neutral 0.1 mM EDTA. The solution was sealed inside a siliconized glass capillary tube (Brand micro-pipette, 5–50 ul), cooled in an ice-water bath 10 cm below a sunlamp (Philips Ultraphil MLU 300W), and irradiated for 15 Min (see FIG. 3). When 2 ug or more of photobiotin acetate was used, nitrogen bubbles appeared. The solution was then added to 0.1M Tris-HCl pH 9 (50 ul), the volume was increased to 100 ul with water, and the solution was extracted and concentrated with 2-butanol (2×100 ul). The volume of the aqueous phase was increased with water to 35 ul, then 1M sodium acetate (15 ul) and cold ethanol (125 ul) were added, and the biotin-labelled nucleic acid was precipitated by chilling in solid CO$_2$ for 15 min. Centrifugation (Eppendorf microfuge, 4° C., 15 min) yielded a pellet which, when visible, was red. The pellet was washed with cold 70% v/v ethanol, dried in vacuo and dissolved in 0.1 mM EDTA.

Other lamps found to be suitable for photolysis were the Philips HPL-N 400W and the Osram MB/U 400W.

Dot-Blot Hybridization

Heat-sealable polythene bags containing about 0.1 ml of solution/cm$^2$ of nitrocellulose were used for all incubation steps. Nitrocellulose filters (Sartorius, pore size 0.45 um) were soaked in water followed by 20×SSC (SSC: 0.15M NaCl, 0.015M sodium citrate). Dry filters were spotted with nucleic acids in 0.1 mM EDTA (1–2 ul), dried, and baked at 80° C. in vacuo for 2 h. Filters were then pre-hybridized at 42° C. for at least 4 h. in pre-hybridization buffer (50% v/v deionized formamide, 5×SSC, 50 mM sodium phosphate pH 6.5, 0.25 mg/ml sonicated denatured salmon sperm DNA, 0.2%, SDS, 5 mM EDTA and 0.2 mg/ml each of bovine serum albumin, Ficoll 400 and polyvinylpyrrolidone M$_r$ 40,000). Hybridization was carried out in a shaking water bath at 55° C. for 20 h in a buffer containing 4 volumes of pre-hybridization buffer, one volume of 0.5 g/ml sodium dextran sulphate, and 20 ng/ml biotin-labelled M13 DNA probe. Filters were then washed with frequent agitation in 2×SSC, 0.1% SDS (3×15 min, room temp.) and in 0.1×SSC, 0.1% SDS (3×30 min, 55° C.).

Colorimetric Detection

1. Sigma avidin-alkaline phosphatase. Dry filters were incubated at 42° C. for 30 min in STMT buffer (1M NaCl, 0.1M Tris-HCl pH 7.5, 2 mM MgCl$_2$, 0.05% v/v Triton X-100) containing 30 mg/ml bovine serum albumin. After being dried, the filters were incubated at room temp. for 10 min in STMT buffer containing 1 ug/ml of Sigma avidin-alkaline phosphatase and then washed with frequent agitation in STMT buffer (3×10 min) and STM buffer (1M NaCl, 0.1M Tris-HCl pH 9.5, 5 mM MgCl$_2$; 2×5 min). For colour develpment, the filters were incubated at room temp. in the dark with substrate solution (STM buffer, but with only 0.1M NaCl, containing 0.33 mg/ml nitro blue tetrazolium, 0.17 mg/ml 5-bromo-4-chloro-3-indolyl phosphate and 0.33% v/v N,N-dimethylformamide). The reaction was terminated by washing the filters with 10 mM Tris-HCl pH 7.5, 1 mM EDTA.

2. BRL kit. Streptavidin, biotinylated polymer of calf intestinal alkaline phosphatase, 5-bromo-4-chloro-3-indolyl phosphate and nitro blue tetrazolium were used essentially according to the manufacturer's instructions, except that 1M NaCl was substituted for 0.1M NaCl in buffers 1–3 in steps 1–10 of the detection procedure.

3. Enzo Biochem kit. Streptavidin-biotinylated acid phosphatase complex, naphthol AS-MK phosphate and fast violet B salt were used essentially according to the manufacturer's instructions.

Detection of DNP-DMA bound to cellulose nitrate filters

Phage M13 single-stranded DNP-DNA and DNP-bovine serum albumin were spotted on cellulose nitrate filters which were baked at 80° C. for 1 hour in vacuo. Control DNA and protein without DNP groups were also spotted. After equilibration with 3% BSA in a buffered salt solution at 42° C. for 20 min, the filters were washed twice with phosphate buffered saline (PBS)-0.05% Tween 20 and then incubated with appropriately diluted antiDNP antiserum at room temp. for 1 hour. The filters were washed twice for 20 min with PBS-0.5% Tween 20 and then incubated with a commercial preparation of goat-anti-rabbit antibodies coupled to horse radish peroxidase. After 30 min at room temp., the filters were again washed twice with PBS-0.05% Tween 20 and the substrate mixture of 0.5 mg/ml diaminobenzidine, 0.04% CoCl$_2$, 0.1% H$_2$O$_2$, in 0.1M Tris-CHl, pH 7.5, added. Positive colour reactions occurred in 10 min and were only associated with the DNP-DNA and DNP-protein samples spotted on the filters. Hence, the DNP-antibodies prepared against DNP-protein also react with DNP-DNA prepared using photo-DNP.

In the following discussion, there is reference to FIGS. 3 to 6.

Figure 3:
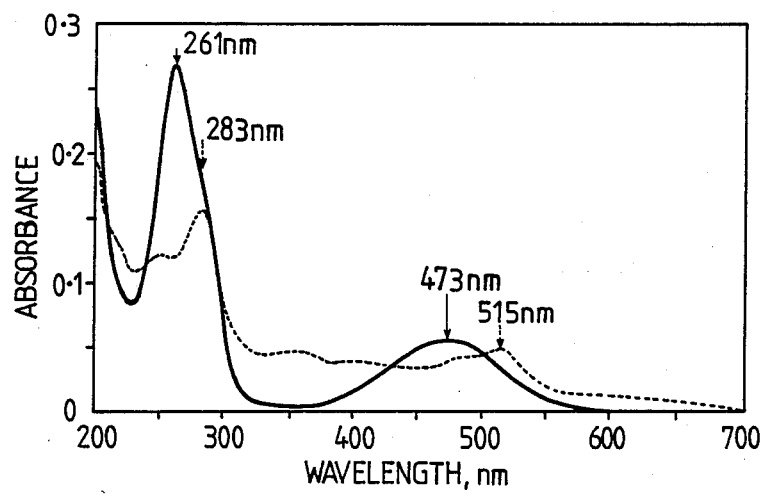

FIG. 3 Absorbance spectrum of photobiotin acetate before and after photolysis. An aqueous solution of photobiotin acetate (0.5 ug/ul, 20 ul) was diluted with water to a volume of 1.2 ml for spectral analysis before (solid line) and after (broken line) photolysis as above.

Figure 4:
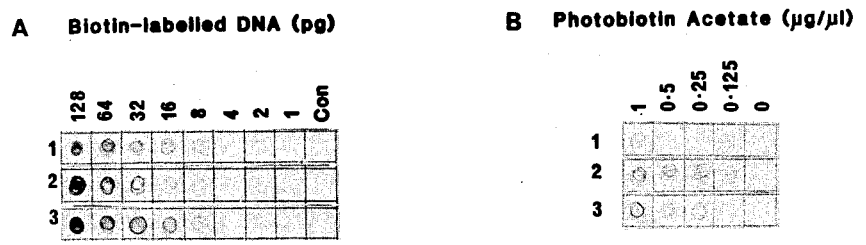

FIG. 4 Colorimetric detection with three commercial enzyme complexes of biotin-labelled DNA bound to nitrocellulose. (A) Variation of amount of DNA per spot to determine sensitivity of detection. Single-stranded M13 DNA was labelled with photobiotin acetate, spotted and baked on nitrocellulose, and detected. Con is a control of 128 pg of M13 DNA. Detection systems and reaction times were: Lane 1: Enzo Biochem streptavidin-biotinylated acid phosphatase, overnight; Lane 2: BRL streptavidin and biotinylated alkaline phosphatase polymer, 5 h; Lane 3: Sigma avidin-alkaline phosphatase, 5 h. (B) Effect of extent of biotin-labelling of DNA on the relative sensitivity of detection. M13 DNA was labelled with photobiotin acetate at final concentrations given. Samples (20 pg) of each DNA were spotted and baked on nitrocellulose, and detected as in (A), except the reaction time for Lane 2 was overnight.

Figure 5:
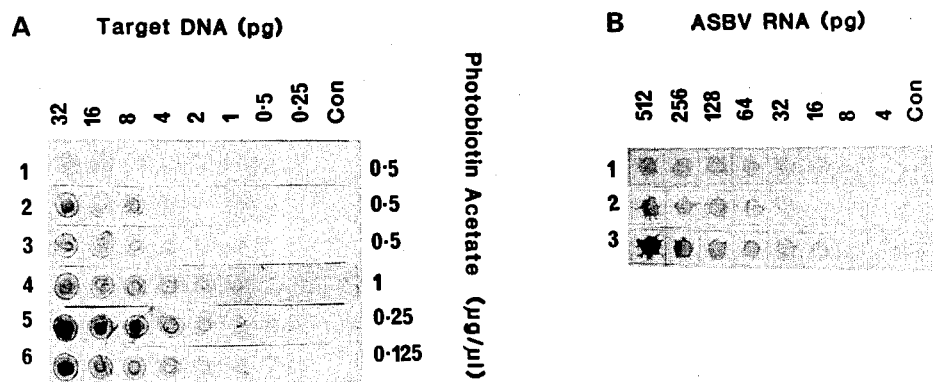

FIG. 5 Colorimetric detection with three commercial enzyme complexes of biotin-labelled DNA probes after hybridization to target nucleic acids bound to nitrocellulose. (A) Variation of amount of cloned ASBV DNA per spot to determine sensitivity of detection. Samples of a single-stranded M13 DNA plus clone of ASBV containing given amounts of target insert DNA were spotted and baked on nitrocellulose. Con is a control of 1 ng of M13 DNA. Probes were prepared by labelling an M13 DNA minus clone of ASBV with photobiotin acetate at final concentrations given. Prehybridization, hybridization and detection were as described above. Detection systems and reaction times were: Lane 1: Enzo Biochem enzyme complex, overnight; Lane 2: BRL enzyme complex, 5 h; Lanes 3–6; Sigma enzyme conjugate, 5 h. (B) Variation of amount of ASBV RNA per spot to determine sensitivity of detection. Samples (amounts given) of purified ASBV were spotted and baked on nitrocellulose. Con is a control of 512 pg of yeast low molecular weight RNA. Detection was the same as in (A), Lanes 1–3.

Figure 6:
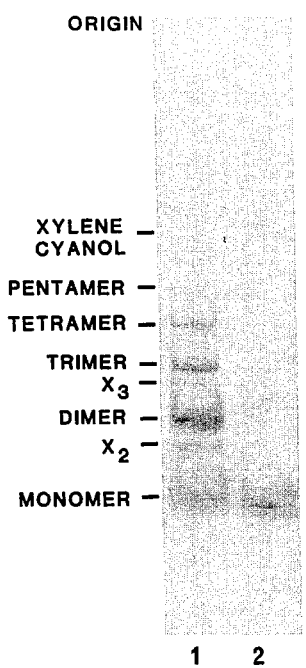

FIG. 6 Northern hybridization analysis of plus ASBV sequences in a partially purified nucleic acid extract of infected avocado leaves. Extract (lane 1, 5 ug) were glyoxalated, electrophoresed in a 1.9% agarose gel and transferred to nitrocellulose. A biotin-labelled M13 DNA minus clone of ASBV was used for hybridization and the Sigma enzyme complex for colorimetric detection (2h reaction). Positions of prominent bands and marker dye are labelled.

LABELLING OF NUCLEIC ACIDS WITH PHOTOBIOTIN ACETATE

Nucleic acids were usually sealed inside glass capillary tubes to minimise potential damage by ultra-violet light during photolysis. To determine the degree of labelling of nucleic acids with photobiotin, $^{14}$C-photobiotin acetate was synthesized from d-(carbonyl-$^{14}$C)biotin (58 mCi/mmol; Amersham) by a microscale adaption of the preparative procedure in Materials and Methods. When $^{14}$C-photobiotin acetate (0.5 ug/ul) was photolysed with single-stranded phage M$_{13}$ DNA (0.5 ug/ul) in 0.05 mM EDTA (5 ul) and the biotin-labelled DNA purified as in Materials and Methods, about seven biotins were bound per 1000 residues. Control experiments in which $^{14}$C-photobiotin acetate was photolysed before mixing with the DNA showed that the purification procedure removed all photolysed photobiotin not coupled to the DNA.

The number of biotins on the DNA accessible for binding to avidin was determined by adding an excess of avidin to biotin-labelled M13 DNA (bio-M13 DNA), separating the avidin-bio-M13 DNA complexes from excess avidin by gel filtration (HPLC on a TSDK 3000 SW column buffered with 1M NaCl, 50 mM sodium phosphate pH 7, and measuring the change in absorbance at 215 nm of the bio-M13 DNA and avidin fractions. When M13 DNA (0.5 ug/ul was labelled with photobiotin acetate at concentrations of 0.125, 0.25, 0.5 and 1 ug/ul in 0.05 mM EDTA, about 2.5, 4, 7 and 10 avidins were bound per 1000 residues. These estimates were considered to be approximate due to the incomplete recovery of the components from the column. On the assumption that each avidin, which has four biotin-binding sites, was coupled to only one biotin, and that all biotins were bound, these estimates correspond to the number of biotins coupled per 1000 residues of DNA. The results were consistent with the relative colour intensities of the red bio-$M_{13}$ DNA pellets after ethanol precipitation and with the estimate obtained by labelling with $^{14}C$-photobiotin. As final concentrations of photobiotin acetate of 2 ug/ul (1.2 molar excess over DNA residues) or more caused the precipitation of the DNA salt of photobiotin, both photobiotin acetate and nucleic acid were used at 0.5 ug/ul for the routine preparation of probe.

The labelling procedure has been used with 1-25 ug of single-stranded M13 DNA and is suitable for the preparation of biotin-labelled probe on a much larger scale. When 15 ug or more of DNA was labelled, a red pellet was clearly visible after ethanol precipitation. Double-stranded DNA and single-stranded RNA were also labelled efficiently by the same procedure as indicated by red nucleic acid pellets and colorimetric detection (see below) on nitrocellulose filters.

The labelling of single-stranded, circular M13 DNA with photobiotin had little effect on the integrity of the DNA as shown by electron microscopy. Thus, DNA containing 100% circular molecules gave a biotin-labelled product with 70% circular, 25% full-length linear and 5% less than full-length linear molecules.

The covalent linkage between the M—DNA and biotin was stable to the usual conditions for immobilization on nitrocellulose and for hybridization reactions as shown by dot-blot hybridization experiments. Samples of bio-M13 DNA were spotted on nitrocellulose and baked at 80° C. in vacuo for 0.5 to 4 h. In addition, other samples, after being baked for 2 h. were incubated for 4 h at 55° C. in pre-hybridization buffer followed by 20 h at 65° C. in hybridization buffer. All these samples gave the same colour response with Sigma avidin-alkaline phosphatase (see below) indicating that there was no loss of DNA-coupled biotin under any of the conditions used. Hybridization experiments (see below) indicated that solutions of bio-M13 DNA probe in 0.1 mM EDTA were stable for at least five months at −15° C.

STABILITY OF BIOTIN COUPLED TO PHAGE M13 SINGLE-STRANDED DNA

Biotin-labelled M13 DNA prepared by the standard procedure was heated at 100° C. in 10 mM Tris-HCl, 0.1 mM EDTA, pH 8, for various periods up to 60 min or incubated in 0.5 N NaOH at 25° C. for periods up to 30 min. Samples were diluted with 0.1M Na acetate and samples of 3 ul at various DNA concentrations spotted on cellulose nitrate. After baking at 80° C. in vacuo to immobilize the DNA, the colorimetric detection of photobiotin-labelled DNA using Sigma avidin-alkaline phosphatase was carried out. There was no difference in the ability to detect DNA in any sample down to 5 pg per spot. Hence, the biotin linkage to DNA was stable under the conditions used.

COLORIMETRIC DETECTION OF PHOTOBIOTIN-LABELLED NUCLEIC ACIDS SPOTTED ON NITROCELLULOSE

Nitrocellulose filters were spotted with bio-M13 DNA, baked, and then subjected to the three colorimetric detection procedures described in Materials and Methods without going through the pre-hybrization and hybridization steps. The Sigma avidin-alkaline phosphatase conjugate, the BRL streptavidin, an avidin-like protein, and biotinylated alkaline phosphatase polymer and the Enzo Biochem streptavidin-biotinylated acid phosphatase complex all gave similar lower sensitivities of detection of about 4 pg ($2 \times 10^{-~mol}$) of bio-M13 DNA. The alkaline phosphatase complexes reached maximum sensitivity faster (5 h) than the acid phosphatase complex (overnight).

The unexpected result of FIG. 4A, lane 3, was that the Sigma conjugate, which had 2.1 mole alkaline phosphatase per mole avidin as well as deoxy-ribonuclease activity (results not given), was as sensitive as the BRL polymeric enzyme complex (FIG. 4A, lane 2). However, the relative sensitivity of detection of bio-M13 DNA by the three enzyme complexes was dependent on the extent of labelling of the M13 DNA with biotin (FIG. 4B). For the Enzo Biochem and Sigma complexes (FIG. 4B, lanes 1 and 3, respectively), colour intensity was roughly proportional to the concentration of photobiotin acetate used to prepare the bio-M13 DNA and hence to the extent to labelling of the DNA with biotin (see above). The dot-blot procedure, when used with these two complexes, could therefore be useful for the relative estimation of the degree of labelling of nucleic acids with photobiotin. By contrast, there was little variation in colour intensity with the degree of biotin-labelling of DNA when the BRL polymeric enzyme complex was used (FIG. 4B, lane 2). Hence, this enzyme complex appears to be the most sensitive for detecting DNA labelled to a low extent with biotin.

Since avidin is a very basic protein, it is electrostatically attracted to nucleic acids. Hence, 1M NaCl was needed in the colorimetric detection buffers to reduce non-specific background colour by dissociating ionic interactions. The kits from Enzo Biochem and BRL employ the biotin-binding protein, streptavidin, instead of avidin because it has an acidic isoelectric point and is therefore not electrostatically attracted to nucleic acids.

The Enzo Biochem streptavidin-horse radish peroxidase complex (Detek 1 hrp, #EBP-820), when used with hydrogen peroxide and diaminobenzidine substrates essentially according to the manufacturer's instructions, had a lower limit of detection of 30 pg of bio-M13 DNA (results not given). The Sigma avidin-peroxidase conjugate (# A3151), when used under the same conditions, was even less sensitive but the limit of detection was not determined. These results, together with those of Leary et al. show that alkaline phosphatase complexes are more sensitive than horse radish peroxidase complexes.

COLORIMETRIC DETECTION OF PHOTOBIOTIN-LABELLED NUCLEIC ACID PROBES AFTER HYBRIDIZATION TO IMMOBILIZED NUCLEIC ACIDS

Nitrocellulose filters were spotted with M—DNA plus clones of ASBV, baked, pre-hybridized, and then hybridized with a bio-M—DNA minus clone of ASBV. The three colorimetric detection procedures all gave similar lower sensitivities of detection of about 0.5 pg ($6 \times 10^{-18}$ mol) of target ASBV sequence (FIG. 5A, lanes 1-3). The alkaline phosphatase complexes (lanes 2 and 3) reached maximum sensitivity faster (5 h) than the acid phosphatase complex (lane 1, overnight). Bio-M13 DNA probes labelled with photobiotin acetate at concentrations of 0.125-1 ug/ul gave similar lower levels of detection with the Sigma avidin-alkaline phosphatase (FIG. 5A, lanes 3-6). This result was unexpected in view of the result obtained for the detection of samples of bio-M13 DNA spotted directly on nitrocellulose (FIG. 4B, lane 3) and suggests that an increase in sensitivity would not be achieved using probes labelled to a higher extent with biotin.

The bio-M13 DNA minus probe was also hybridized to samples of the RNA, ASBV, spotted on nitrocellulose (FIG. 5B). The lower sensitivity of detection of about 4 pg of ASBV is equivalent to that obtained with single-stranded $^{32}$P-labelled M13 DNA probes. Preliminary attempts to apply bio-M13 DNA probes to the diagnosis of ASBV in avocado trees have not been successful so far. When partially purified nucleic acid extracts of leaves from various healthy avocado trees were prepared and spotted on nitrocellulose as in Barker et al., (1985) some of the sample bound the bio-M13 DNA probe during hybridization, leading to false positives. Since the probe did not bind to purified coconut cadang cadang viroid (100 ng RNA/spot), tobacco mosaic virus RNA (5 ug/spot), chick embryo poly (A)+ RNA (2.5 ug/spot) or sheared salmon sperm DNA (5 ug/spot) (results not given), false positives were presumably due to the binding of the probe to non-nucleic acid material in the partially purified extracts.

Bio-M13 DNA probes have been used successfully for the detection of specific RNA sequences by Northern hybridization analysis (FIG. 6). A partially purified nucleic acid extract of avocado leaves infected with ASBV was glyoxalated, electrophoresed in an agarose gel, transferred to nitrocellulose and probed with a bio-M13 DNA minus clone of ASBV. Colorimetric detection with the Sigma enzyme conjugate produced a pattern of oligomeric forms (dimer to pentamer) in addition to the monomeric, 247 residue ASBV, as well as two minor bands labelled $X_2$ and $X_3$ (FIG. 6). The pattern and sensitivity of detection were equivalent to those obtained using a single-stranded $^{32}$P-labelled DNA probe.

The extent of background colour was dependent on the concentration of bio-M13 DNA probe used in the hybridization mixture. While probe concentrations of 100-1000 ng/ml gave unacceptable backgrounds, insignificant backgrounds were obtained by reducing the probe concentration to 20 ng/ml. These backgrounds may be a property of the M13 DNA since biotin-labelled, double-stranded DNA and single-stranded RNA probes have been used at a concentration of 100 ng/ml without significant backgrounds (results not given).

LABELLING OF PROTEINS WITH PHOTOBIOTIN ACETATE

Since aryl nitrenes can react with a wide range of functional groups including protein groups, photobiotin was considered to be a potential new reagent for the rapid labelling of proteins with biotin. A solution of photobiotin acetate (10 ug/ul) and a mixture of bovine intestinal alkaline phosphatase (85-90% of total protein) and bovine serum albumin (1 ug/ul; Sigma #P0655) in 5 mM NaCl, 0.05 mM $ZnCl_2$ (50 ul) was sealed in a glass capillary tube and irradiated for 30 min as described for nucleic acids. 2-Butanol (50 ul) was added, followed by 0.1M Tris-HCl pH 9 (100 ul) and the aqueous phase was extracted three times with 2-butanol. A gel filtration assay, similar to that described above, showed that there were about five biotins per molecule of alkaline phosphatase ($M_r$ 100,000) accessible for binding to avidin. The activity of the enzyme was essentially unchanged by this treatment. It was necessary to remove the Tris-citrate buffer salts from the commercial enzyme by dialysis prior to photolysis, since these presumably acted as scavengers for the photogenerated aryl nitrene.

The process described here for the preparation of stable, non-radioactive hybridization probes overcomes at least some of the disadvantages of prior art labelling procedures. The method is rapid, reliable and safe, and allows the inexpensive, small- or large-scale labelling of any single- or double-stranded DNA or RNA with biotin. The labelled nucleic acid is easily purified from uncoupled reagent, and the labelling can be monitored visually because photobiotin-labelled nucleic acid is red. Single-stranded DNA is not degraded or cross-linked by the labelling procedure. The recommended labelling of nucleic acids to the extent of one biotin per 100-400 residues is unlikely to interfere with the recognition of complementary sequences by the probe. Biotin-labelled DNA probes are stable under standard hybridization conditions and give reproducible results in hybridization reactions over a period of at least five months.

Single-stranded M13 DNA probes labelled with one biotin per 100-400 residues detected as little as 0.5 pg ($6 \times 10^{-18}$ mol) of target DNA in dot-blot hybridization reactions on nitrocellulose using alkaline or acid phosphatase complexes from Sigma, BRL or Enzo Biochem (FIG. 5A). The detection of target RNA in dot-blots (FIG. 5B) and Northern blots (FIG. 6) was equivalent in sensitivity to radioactive methods. In contrast to the results of Leary et al. simple avidin-alkaline phosphatase conjugates were found to be as sensitive as polymeric enzyme complexes.

Photobiotin-labelled probed may be applied to the routine diagnosis of plant and animal diseases, hybridizaiton in situ, the enrichment of specific nucleic acids from mixtures by hybrid selection and the enrichment of specific nucleic acid-bind proteins. The labelling procedure is particularly suitable for hybrid-selection reactions requiring large amounts of probe.

Photobiotin acetate can also be used as a protein-labelling reagent. It provides an alternative to other reagents for the labelling of proteins with biotin which are used in aqueous organic solvents. In addition, $^3$H- or $^{14}$C-photobiotin may be used for the photoaffinity labelling of biotin-binding proteins.

I claim:

1. A compound of the Formula I

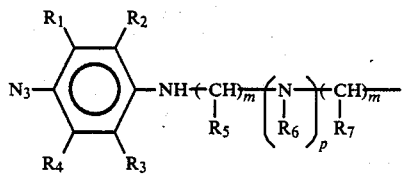

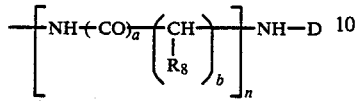

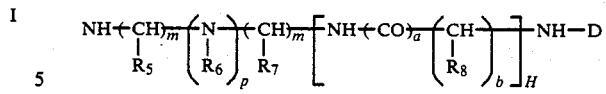

in Formula I is selected from the group consisting of:

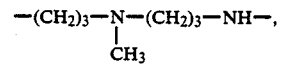

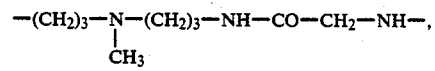

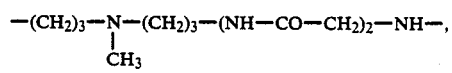

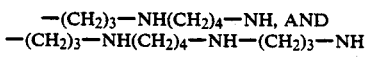

6. A compound according to claim 4 wherein the group

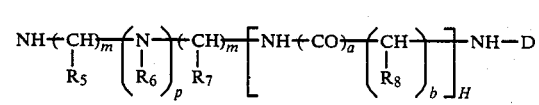

in Formula I is selected from the group consisting of

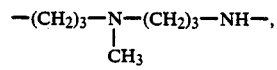

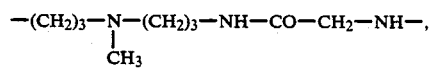

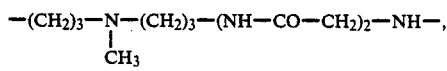

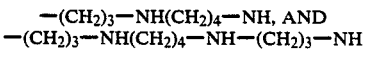

wherein $R_1$ to $R_4$, which may be the same or different, are selected from the group consisting of H, alkyl of 1 to 5 carbon atoms, $NO_2$, halogen, —COOH, and —$NH_2$;
wherein $R_5$, $R_6$, $R_7$, $R_8$ which may be the same or different are selected from the group consisting of H, alkyl of 1 to 5 carbon atoms and halogen; wherein
n is an integer of 0 to 5
m is an integer of 1 to 10
p is an integer of 0 to 1
a is an integer of 0 to 1
b is an integer of 1 to 10
wherein if a is 1 then b is 1, and
wherein the moiety

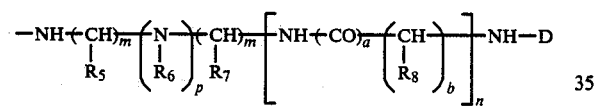

includes at least 5 carbon atoms and wherein D is selected from the group consisting of

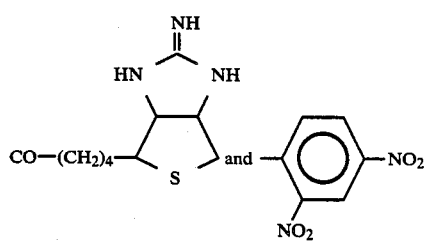

2. A compound according to claim 1 wherein D is

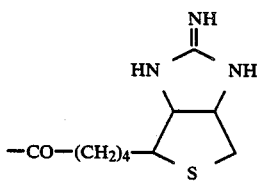

3. A compound according to claim 1 wherein each of $R_1$ to $R_4$ is hydrogen.

4. A compound according to claim 1 wherein $R_1$, $R_2$ and $R_4$ are hydrogen and $R_3$ is —$NO_2$.

5. A compound according to claim 3 wherein the group

7. A compound of the Formula I

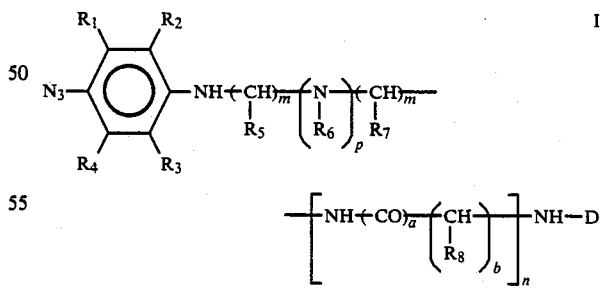

wherein $R_1$ to $R_4$, which may be the same or different, are selected from the group consisting of H, alkyl of 1 to 5 carbon atoms, $NO_2$, halogen, —COOH, and —$NH_2$;
wherein $R_5$, $R_6$, $R_7$, $R_8$ which may be the same or different are selected from the group consisting of H, alkyl of 1 to 5 carbon atoms and halogen wherein
n is an integer of 0 to 5
m is an integer of 1 to 10
is an integer of 0 to 1 a is an integer of 0 to 1
b is an integer of 1 to 10,
wherein if a is 1 then b is 1, and
wherein the moiety
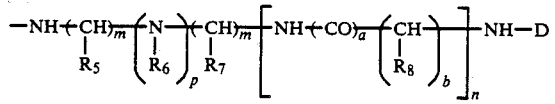
includes at least 5 carbon atoms; and D is
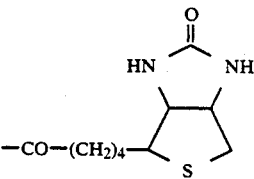
8. A compound selected from the group consisting of
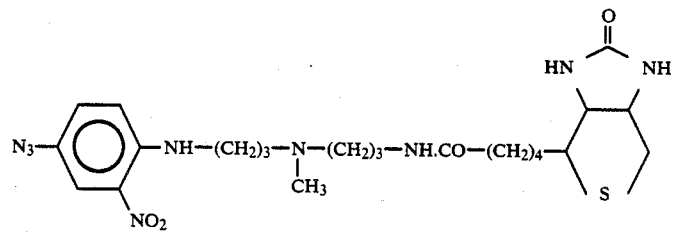
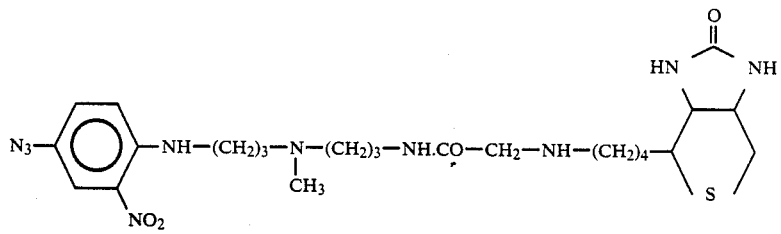
* * * * *